United States Patent [19]

Jacobsen et al.

[11] Patent Number: 5,504,085
[45] Date of Patent: Apr. 2, 1996

[54] TRIAZOLO QUINOXALINES AND THEIR PREPARATION AND USE

[75] Inventors: Poul Jacobsen, Rødovre; Flemming E. Nielsen, Virum, both of Denmark

[73] Assignee: Novo Nordisk A/S, Novo Alle, Denmark

[21] Appl. No.: 285,598

[22] Filed: Aug. 3, 1994

Related U.S. Application Data

[63] Continuation of Ser. No. 944,151, Sep. 11, 1992, abandoned.

[30] Foreign Application Priority Data

Sep. 20, 1991 [DK] Denmark .................... 1624/91

[51] Int. Cl.$^6$ .................... A61K 31/495; C07D 487/04; C07D 241/52
[52] U.S. Cl. ................ 514/250; 544/346; 544/354
[58] Field of Search ................ 544/346; 514/250

[56] References Cited

U.S. PATENT DOCUMENTS

| | | | |
|---|---|---|---|
| 4,354,027 | 10/1982 | Loev | 544/346 |
| 4,400,382 | 8/1983 | Brown et al. | 424/250 |
| 4,623,725 | 11/1986 | Kadin | 544/346 |
| 4,780,464 | 10/1988 | Trivedi | 544/346 |
| 4,975,430 | 12/1990 | Jahr | 514/255 |

FOREIGN PATENT DOCUMENTS

| | | |
|---|---|---|
| 92-07847 | 5/1992 | WIPO. |
| 93-08173 | 4/1993 | WIPO. |
| 93-21171 | 10/1993 | WIPO. |

OTHER PUBLICATIONS

Goldberg, *Neuroscience Letters* 23, 187–191 (1981).
Turski II, *Neuroscience Letters* 53, 321 (1985).
Sheardown Science 247, p. 571 (1990).
Davies J. Physiol. 297, 621 (1979).
Nellgard, Exp. Brain Res 92, 259–266 (1992).
Wrathall, Brain Res 586, 140 (1992).
Croucher, *Science* 216, 899 (1982).
Turski, I, *Nature* 349, 414 (1991).
Stephens, *Psycho pharmacology* 85, 143–147 (1985).
Simon, Science 226, p. 850 (1984).
Wieloch, Science 230, 681 (1985).
Faden, Science 244, (1989) p. 799.
Cammalm, Nature 263, p. 517 (1976).
Benveniste, J. Neurochem. 43, 1369 (1984).
Koshel, Chem Abs 73, 120589c (1970).
Loev et al., J. Med. Chem., vol. 28, pp. 363–366 (1985).
Stephens et al., Psychopharmacology, vol. 85, pp. 143–147 (1985).
Khandwala et al., Int. Archs Allergy appl. Immun., vol. 73, pp. 56–64 (1984).
Faden et al., Science, vol. 244, pp. 798–800 (1988).
McGeer et al., Nature, vol. 263, pp. 517–519 (1976).
M. J. Croucher et al., Science, vol. 216, pp. 899–901 (1982).

*Primary Examiner*—Mark L. Berch
*Attorney, Agent, or Firm*—Steve T. Zelson; Elias J. Lambiris

[57] ABSTRACT

Quinoxaline compounds represented by formulas I or II,

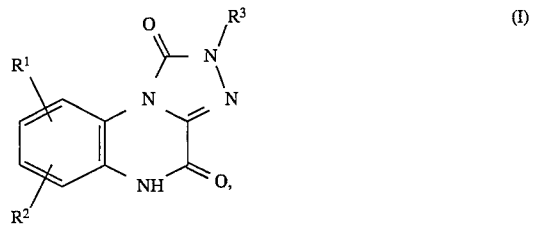

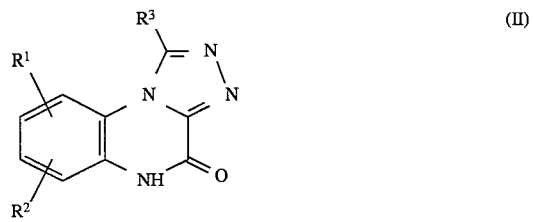

wherein $R^1$ and $R^2$ are independently hydrogen, $C_{1-6}$-alkyl, halogen, $NO_2$, $NH_2$, CN, $CF_3$, $SO_2NR^4R^5$ wherein $R^4$ and $R^5$ are independently hydrogen or $C_{1-6}$-alkyl, or $COR^6$ wherein $R^6$ is $C_{1-6}$-alkyl; and $R^3$ is hydrogen, $C_{1-6}$-alkyl or $CF_3$, compositions thereof and methods of preparing the compounds are described.

The compounds are useful in the treatment of indications caused by hyperactivity of the excitatory neurotransmitters.

24 Claims, No Drawings

TRIAZOLO QUINOXALINES AND THEIR PREPARATION AND USE

This application is a continuation application of application Ser. No. 07/944,151, filed Sept. 11, 1992, the contents of which are incorporated herein by reference.

The present invention relates to therapeutically active heterocyclic compounds, a method of preparing the same, pharmaceutical compositions comprising the compounds, and a method of treating therewith.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent anxiolytic (Stephens et al., Psychopharmacology 85, 143–147, 1985), anticonvulsant (Croucher et al., Science 216, 899–901, 1982) and muscle relaxant properties (Turski et al., Neurosci. Lett. 53, 321–326, 1985).

It has been suggested that accumulation of extracellular excitatory amino acids, followed by overstimulation of neurons, may explain the neuronal degenerations seen in neurological disorders such as amyotrophic lateral sclerosis, Parkinsonism, Aizheimer's disease, Huntington's disease, epilepsy, and deficiencies of mental and motor performance seen after conditions of brain ischemia, anoxia and hypoglycemia or head and spinal cord trauma (McGeer et al., Nature 263, 517–519, 1976; Simon et al., Science 226, 850–852, 1984; Wieloch, Science 230, 681–683, 1985; Faden et al., Science 244, 798–800, 1989; Turski et al., Nature 349, 414–418, 1991). Other possible indications are psychosis, muscle rigidity, emesis and analgesia.

Excitatory amino acids exert their actions via specific receptors located postsynaptically or presynaptically. Such receptors are at present conveniently subdivided into three groups bases on electrophysiological and neurochemical evidence: 1 the NMDA (N-methyI-D-aspartate) receptors 2 the AMPA receptors, and 3 the kainate receptors. L-glutamic acid and L-asparartic acid probably activate all the above types of excitatory amino acid receptors and possibly other types as well.

The above mentioned classification of excitatory amino acid receptors into NMDA, AMPA, and kainate receptors is based primarily on the following electrophysiological and neurochemical findings.

1) N-methyl-D-aspartate (NMDA) receptors exhibit high selectivity for the excitant NMDA. Ibotenic acid. L-homocysteic acid, D-glutamic acid and trans-2,3-piperidine dicarboxylic acid (trans-2.3-PDA) exert a strong to moderate agonist activity on these receptors. The most potent and selective antagonists are the D-isomers of the 2-amino-5-phosphonocarboxylic acids. e.g. 2-amino-5-phosphono-valedc acid (D-APV) and 3-[(±)-2-carboxypipetazin- 4-yl]-propyl-1-phosphonic acid (CPP), while moderate antagonist activity is shown by the D-isomers of long chain 2-amino dicarboxylic acids (e.g. D-2-amino-adipic acid) and long chain diaminodicarboxylic acids (e.g. diaminopimelic acid). The NMDA-induced synaptical responses have been extensively investigated in the mammalian CNS, especially in the spinal cord (J. Davies et al., J. Physiol. 297, 621–635, 1979) and the responses have been shown to be strongly inhibited by $Mg^{2+}$.

2) AMPA receptors are activated selectively by AMPA (2-amino-3-hydroxy- 5-methyl-4-isoxazolepropionic acid), other potent agonists being quisqualic acid and L-glutamic acid. Glutamic acid diethyl ester (GDEE) is a selective but very weak antagonist of this site. AMPA receptors are relatively insensitive to $Mg^{2+}$.

Glutamate release has long been thought to play a major role in neuronal death resulting from cerebral ischemia (Benveniste, H. et al., J. Neurochem. 43, 1369–1374, 1984). It is well known that NMDA receptor evoked $Ca^{2+}$ influx is an important mechanism in ischemic neuronal cell loss. The nonNMDA receptor coupled ionophor is not permeable to calcium. However, the excitation by the Scaffer collaterals in the CA 1 region is excerted by non-NMDA receptors, and this fact is of importance for the events in the postischemic period. Recent studies have shown that selective AMPA antagonists have neuroprotectant effects in global ischemia in the gerbil even when given several hours after reperfusion (Sheardown et al., Science 247, 571–574, 1990).

AMPA antagonists are therefore useful in the treatment of cerebral ischemia.

3) Kainate receptors. Excitatory responses to kainic acid are relatively insensitive to antagonism by NMDA-antagonists and by GDEE, and it has been proposed that kainic acid activates a third subclass of acidic amino add receptor. Certain lactonized derivatives of kainic acid are selective antagonists (O. Goldberg et al., Neurosi. Lett. 23, 187–191, 1981) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essense, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

AMPA receptor binding may be studied by using $^3$H-AMPA as radioligand.

The influence of glutamic add analogues on secondary effects of glutamate receptor interactions may be studied in vitro by using the phenomenon of spreading depression in chicken retina. Such experiments will provide information as to the efficades (agonist/antagonist) of the test substances. This is in contrast to binding studies, which only provide information on the affinities of the compounds for the receptor.

It has now been found that the compounds of the invention have affinity for the AMPA receptors and are antagonists in connection with this type of receptor which makes them useful in the treatment of any of the numerous indications caused by hyperactivity of excitatory amino adds.

In U.S. Pat. No. 4,400,382 1-oxo-1H,4H(1,2,4)triazolo(4,3-a)-quinoxaline-4one is described as possessing useful anti-allergic activity.

The compounds of the invention are represented by the general formulas I and II

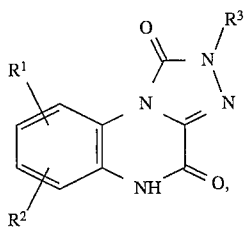 (I)

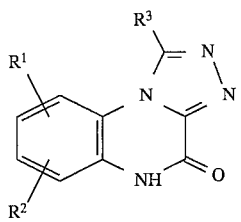 (II)

wherein

R$^1$ and R$^2$ are independently hydrogen, C$_{1-6}$-alkyl, halogen, NO$_2$, NH$_2$, CN, CF$_3$, SO$_2$NR$^4$R$^5$ wherein R$^4$ and R$^5$ are independently hydrogen or C$_{1-6}$-alkyl, or COR$^6$ wherein R$^6$ is C$_{1-6}$-alkyl; and R$^3$ is hydrogen, C$_{1-6}$-alkyl or CF$_3$, and pharmaceutically acceptable salts thereof.

The invention also relates to a method of preparing the above-mentioned compounds. The present compounds of formula I are prepared by a) reacting a compound having the formula III

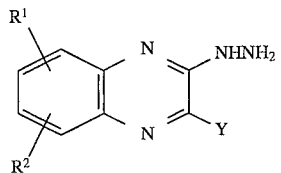 (III)

wherein R$^1$ and R$^2$ have the meanings defined above and Y is halogen or C$_{1-6}$-alkoxy with phosgene or a reactive equivalent thereof to form a compound of formula IV

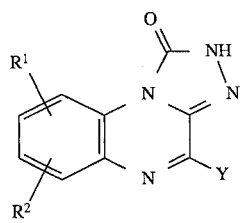 (IV)

wherein R$^1$, R$^2$ and Y have the meanings defined above, and hydrolyzing the compound of formula IV to form a compound of formula I, or b) alkylating a compound having the formula IV with a compound having the general formula V

R$^3$—X (V)

wherein R$^3$ has the meaning defined above and X is a leaving group, to form a compound of formula VI

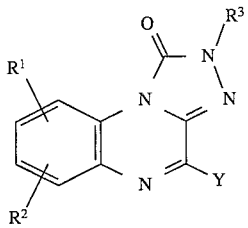 (VI)

wherein R$^1$, R$^2$ and R$^3$ have the meanings defined above, and hydrolyzing the compound under conventional conditions to form a compound of formula I or c) alkylating a compound having the formula VII

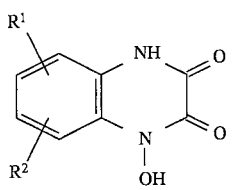 (VII)

wherein R$^1$ and R$^2$ have the meanings defined above with benzyl halogenide to form a compound of the formula VIII

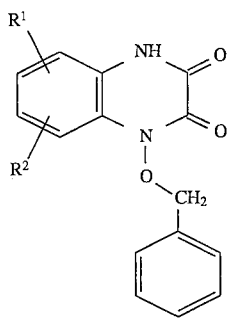 (VIII)

wherein R$^1$ and R$^2$ have the meanings defined above and reacting the compound with phosgene or a reactive equivalent thereof in N,N-dimethylformamide to form a compound of the formula IX

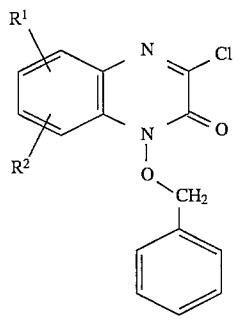 (IX)

wherein R$^1$ and R$^2$ have the meanings defined above and reacting the compound of formula IX with a compound having the general formula X

NH$_2$NHCOOR$^7$ (X)

wherein $R^7$ is $C_{1-6}$-alkyl to form a compound of formula XI

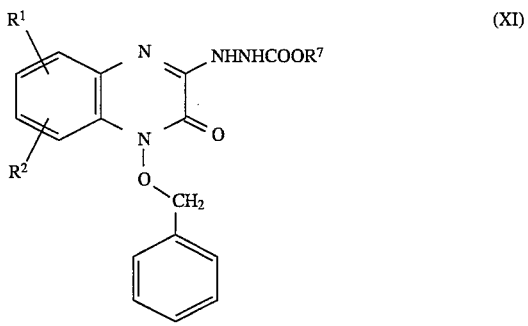

wherein $R^1$, $R_2$ and $R^7$ have the meanings defined above, and hydrogenolysis of the compound to form a compound of the formula XII

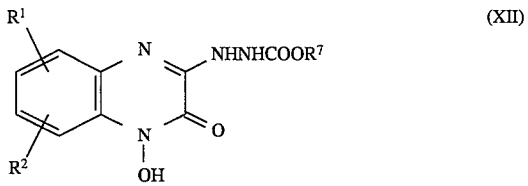

wherein $R^1$, $R^2$ and $R^7$ have the meanings defined above, and then either thermal cyclization and simultaneous deoxygenation or basic cyclization under aqueous basic conditions and subsequent deoxygenation to form a compound of formula I, Compounds of formula II are obtained by reacting a compound having the formula III with a compound having the general formula XIII $$R^8\text{-C}(OC_2H_5)_3 \qquad (XIII)$$

wherein $R^8$ is hydrogen or $C_{1-6}$-alkyl, or with trifluoroacetic acid to form a compound having the formula XIV

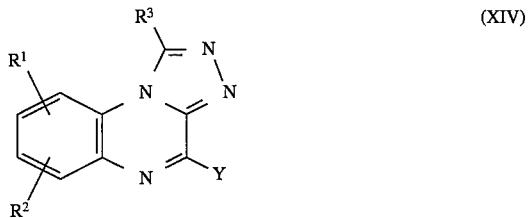

wherein $R^1$, $R^2$, $R^3$ and Y have the meanings defined above, and hydrolyzing the compound of formula XIV under conventional conditions to form a compound of formula II.

The pharmacological properties of the compounds of the present invention can be illustrated by determining their capability for displacing radioactively labelled 2-amino-3-hydroxy-5-methyl-4-isoxazolepropionic acid (AMPA) from the AMPA type receptors. The antagonistic properties of the compounds is demonstrated by their capability to antagonize quisqualic acid stimulated spreading depression in chicken retina.

The displacement activity of the compounds may be shown by determining the $IC_{50}$ value which represents the concentration (μ g/ml) which causes a displacement of 50% of the specific binding of $^3$H-AMPA.

The antagonism is measured by determining the $IC_{50}$ value which represents the concentration which produces a ,50% maximal inhibition of quisqualic acid stimulated spreading depression in chicken retina.

$^3$H-AMPA binding (Test 1)

500 μl of thawed rat cerebral cortical membrane homogenate in Tris-HCl (30 mM), $CaCl_2$ (2.5 mM) and KSCN (100 mM) pH 7.1 were incubated at 0° C. for 30 min. with 25 μl $^3$H-AMPA (5 nM final concentration) and the test compound and buffer. Non specific binding was determined by incubation with L-glutamic acid (600 μ mM final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Spreading depression (Test 2)

Chicks (3–10 days old) were decapitated, the eyes enucleated and sectioned along the equatorial plane. After removal of the anterior chamber and the vitreous body, the posterior chamber of each eye was placed in a small petri dish containing a physiological saline solution (P.S.S.) of the following composition (mM) NaCl (100), KCl (6.0), $CaCl_2$ (1.0), $MgSO_4$ (1.0), $NaHCO_3$ (30), $NaH_2PO_4$ (1.0), glucose (20).

The solution was saturated with 100% $O_2$ and maintained at 26° C.

The eyes are initially incubated in normal P.S.S. for 15–30 min. and then transferred to P.S.S. containing quisqualate (1μ g/ml). In this "stimulating solution" S.D.'s start spontaneously usually from the edge of the retina, and can be easily observed by eye. The time taken for an S.D. to start in each eye is measured.

After a further 15 min. of incubation in normal P.S.S. the eyes are transferred to normal P.S.S. containing the test compound and incubated for 15 min. Thereafter the eyes are transferred to a "stimulating solution" containing the same concentration of the test compound. The time taken for an S.D. to start in each eye is again measured. The eyes are then placed back in normal P.S.S. and after 15 min. the time taken for S.D. to start is again measured, in order to assess the degree of recovery from any drug effects.

An increase in the time taken for S.D. to start of 30 seconds more than the control time is considered 100% inhibition of S.D. The drug effects therefore are expressed as the percentage maximum response obtained for a given dose. The test value can be quoted therefore as the concentration (μ g/ml) of test substance which produces a 50% maximal inhibition ($IC_{50}$).

Test results obtained by testing some compounds employed in the present invention will appear from the following table 1.

TABLE 1

| Compound of example | TEST 1 $IC_{50}$ μg/ml | TEST 2 $IC_{50}$ μg/ml |
|---|---|---|
| 3 | 1.3 | 1.3 |
| 4 | 0.09 | 0.47 |

The pharmaceutical preparations of compositions comprising the compounds of the invention may be administered to humans or animals by oral or parenteral route.

An effective amount of the active compound or a pharmaceutically acceptable salt thereof may be determined in accordance with the usual factors, such as the nature and severity of the condition and the weight of the mammal requiring treatment.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic add, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains:

| Core: | |
|---|---|
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |
| HPMC approx. | 9 mg |
| *Mywacett ® 9-40T approx. | 0.9 mg |

*Acylated monoglyceride used as plasticizer for film-coating

The free compounds of the present invention which form alkali metal or alkaline earth metal salts may be employed in such salt form. Such alkali metal or earth alkali metal salts are ordinarily formed by reacting the compound with an equivalent amount or excess of the selected alkali metal or earth alkali metal as the hydroxide, frequently and suitably by admixture in the presence of a neutral solvent, from which the salt may be precipitated or recovered in other conventional manner, e.g. by evaporation. Administration of a compound of the invention is often preferably in the form of a pharmaceutically acceptable water-soluble alkali metal or earth alkali metal salt thereof, and orally, rectally or parenterally in the form of a pharmaceutical composition wherein it is present together with a pharmaceutically acceptable liquid or solid carrier or diluent.

The compounds of the invention, together with a conventional adjuvant, carrier or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective AMPA antagonistic amount of the active ingredient commensurate with the intended daily dosage range to be employed. Tablets containing 10 mg to 200 mg of active ingredient or, more specified 50 mg, per tablet, are accordingly suitable representative unit dosage forms.

Due to their high degree of AMPA antagonistic activity and their low toxicity, together presenting a most favourable therapeutic index, the compounds of the invention may be administered to a subject, e.g. a living animal body, in need of such treatment, elimination, alleviation or amelioration of an indication which is sensitive to a change in the AMPA receptor condition, e.g. sclerosis, Parkinsonism, Alzheimer's disease, Huntington's disease, epilepsy, deficiencies seen after ischemia, anoxia, hypoglycemia, head and spinal cord trauma, psychosis, muscle rigidity, emesis and analgesia, often preferably in the form of an alkali metal or earth alkali metal salt thereof, concurrently, simultaneously or together with a pharmaceutically acceptable carrier or diluent, especially and preferably in the form of a pharmaceutical composition thereof whether by oral, rectal, or parenteral (including subcutaneous) route, in an effective amount. Suitable dosage ranges are 10–200 milligrams daily, preferably 50–100 milligrams daily. Band especially 70–100 milligrams daily, depending as usual upon the exact mode of administration, form in which administered, the indication towards which the administration is directed, the subject involved and the body weight of the subject involved, and the preference and experience of the physician or veterinarian in charge. Such method of treating may be described as the treatment of an indication caused by or related to hyperactivity of the excitatory neurotransmitters, and particularly the AMPA receptors in a subject in need thereof, which comprises the step of administering to the said subject a neurologically effective amount of an AMPA antagonistic compound of the invention, or a pharmaceutically acceptable salt thereof.

The invention will now be described in further detail with reference to the following examples:

EXAMPLE 1

8-Chloro[1,2,4]triazolo[4,3-a]quinoxaline-1,4(2H,5H)-dione

A solution of 20% phosgene in toluene (6.3 ml, 12 mmol) was added to a filtered solution of 2.29 g (10 mmol) of crude 2,6-dichloro-3-hydrazinoquinoxaline (R. Sarges et al. J. Med. Chem. 33, 2240 (1990)) in 150 ml of dry tetrahydrofuran, and the mixture was stirred over night at room temperature. After evaporation of solvent, the residue was washed with water to give 2.30 g of crude 4,8-dichloro[1,2,4]triazolo[4,3-a]quinoxalin-1 (2H)-one. The crude intermediate was refluxed in 40 ml of glacial acetic acid for 1 h and the mixture was evaporated to dryness to give 2.16 g of crude dione.

The product was refluxed in 300 ml of ethanol, filtered hot, and the solid residue was dissolved in 25 ml of DMF. The solution was treated with 50 ml of methanol, cooled to precipitate a small amount of impurities, and filtered. The flitrate was treated with 160 ml of water to precipitate a solid, which was dried in vacuo at 125° C. to give 0.66 (28%) of the title compound, m.p. >375° C. dec. (DSC); ¹H-NMR (DMSO-d₆): δ7.22 (d,J=9 Hz, 1H, H-6), 7.38 (dd, J$_{7-6}$=9 Hz, J$_{7-9}$=2 Hz, 1H, H-7), 8.51 (d,J=2Hz, 1H, H-9), 11.88 (br. s, 1H, NH), 13.05 (br. s, 1H, NH); MS (m/e): 238 ((M+2)⁺, 32%), 236 (M⁺, 100%), 180 (20%), 154 (22%), 152 (74%). A second crop (0.65 g, 27%) was obtained from the ethanolic filtrate.

EXAMPLE 2

A. 3-Chloro-2-hydrazino-6-nitroquinoxaline

A mixture of 6.1 g (25 mmol) of 2,3-dichloro-6-nitroquinoxaline and 2.75 g (55 mmol) of hydrazine hydrate in 150 ml of ethanol was stirred at room temperature over night. The precipitate was isolated and washed with water, cold ethanol and ether to give 5.67 g (95%) of crude product.

B. 7-Nitro[1,2,4]triazolo[4,3-a]quinoxaline-1,4(2H,5H)-dione

A mixture of 126 ml (24 mmol) of 20% phosgene in toluene and 4.79 g (20 mmol) of crude 3-chloro-2-hydrazino-6-nitroquinoxaline in 300 ml of dry tetrahydrofuran was stirred over night at room temperature. After evaporation of solvent, the residue was washed with water and finally refluxed in 100 ml of glacial acetic acid for 2 h. The cooled mixture was filtered and the precipitate was washed with acetic acid and ether to give 3.2 g of crude dione. It was then dissolved in 140 ml of DMF, treated with decolourising charcoal, filtered and added 150 ml of methanol. After cooling, a yellow impurity was removed by filtration. The filtrate was treated with 150 ml of water to precipitate the product, which was collected and treated with hot methanol to give 1.48 g (30%) of the title compound; m.p. >412° dec. (DSC); ¹H-NMR (DMSO-d₆): δ8.03 (d,J=2 Hz, 1H, H-6), 8.10 (dd, J$_{8-9}$ =9 Hz, J$_{8-6}$=2 Hz, 1H, H-8), 8.69 (d,J=9 Hz, 1H, H-9), 12.08 (br. s, 1H, NH), 13.13 (br. s, 1H, NH); MS (m/e): 247 (M⁺, 100%), 191 (21%), 163 (29%), 117 (26%), 90 (27%).

The following two examples were prepared in an analogous manner from the appropriate 2,3-dichloroquinoxaline. The 2,3-dichloroquinoxalines were prepared from the corresponding quinoxaline-2,3(1H,4H)-diones in N,N-dimethylformamide by treatment with excess 1.93M phosgene in toluene in a similar way as described in example 12B.

EXAMPLE 3

7-Trifluoromethyl[1,2, 4]triazolo[4,3-a]quinoxaline-1,4(2H, 5H)-dione

M.p. >375° C. (DSC); ¹H-NMR (DMSO-d₆): δ7.51 (s, 1H, H-6), 7.59 (d, J=9 Hz, 1H, H-8), 8.71 (d, J=9 Hz, 1H, H-9), 11.98 (s, 1H, NH), 13.05 (s, 1H, NH). C₁₀H₅F₃N₄O₂ (270) Calc. C 44.46 H 1.87 N 20.74 Found C 44.47 H 1.92 N 20.67

EXAMPLE 4

7-Cyano[1,2,4]triazolo[4,3-a]quinoxaline-1,4(2H, 5H)-dione

M.p. >400° C. (DSC); ¹H -NMR (DMSO-d₆): δ7.56 (d, J=2 Hz, 1H, H-6), 7.69 (dd, J$_{8-9}$=9 Hz, J$_{8-6}$=2 Hz, 1H, H-8), 8.66 (d, J 9 Hz, 1H, H-9), 12.08 (br. s, 1H, NH), 13.10 (br. s, 1H, NH); MS (m/e): 227 (M⁺, 55%).

EXAMPLE 5

A. 3-Chloro-2-methoxy-6-nitroquinoxaline

A slurry of 6.1 g (25 mmol) of 2,3-dichloro-6-nitroquinoxaline in 70 ml of dry methanol was heated to 50° C and treated dropwise over 5 h with 0.7 g (30 mmol) of sodium dissolved in 70 ml of dry methanol. The mixture was stirred over night at 50° C., cooled and filtered. The resulting precipitate was washed with cold ethanol and water and finally chromatographed on silica gel with toluene to give 3.5 g (58%) of the title compound; m.p. 155–158° C.; ¹H-NMR (DMSO-d₆): δ4.17 (s, 3H, CH₃), 8.05 (d,J=9 Hz, 1H, H-8), 8.48 (dd, J$_{7-8}$ =9 Hz, J$_{7-5}$ =2 Hz, 1H, H-7), 8.73 (d, J=2 Hz, 1H, H-5).

B. 3-Hydrazino-2-methoxy-6-nitroquinoxaline

A mixture of 3.4 g (14.2 mmol) of 3-chloro-2-methoxy-6-nitroquinoxaline and 1.65 g (33 mmol) of hydrazine hydrate in 150 ml of ethanol was stirred at room temperature over night. The precipitate was collected and washed with water and cold ethanol to give 3.13 g (94%) of crude product.

C. 8-Nitro[1,2,4]triazolo[4,3-a]quinoxaline-1,4(2H,5H)-dione

A mixture of 8.44 ml (16 mmol) of 20% phosgene in toluene and 3.10 g (13.2 mmol) of 3-hydrazino-2-methoxy-6-nitroquinoxaline in 300 ml of dry tetrahydrofuran was stirred over night at room temperature. The mixture was evaporated to dryness and the solid residue was refluxed for 2.5 h in a mixture of 100 ml of glacial acetic add and 32 ml of 1M hydrochloric acid. The cooled mixture was filtered and the resulting precipitate was washed with acetic acid, water and ethanol to give 1.93 g (59%) of the title compound; m.p. >399° C. dec. (DSC); ¹H-NMR (DMSO-d₆): δ7.36 (d, J=9 Hz, 1H, H-6), 8.20 (dd, J$_{7-6}$ =9 Hz, J$_{7-9}$ =2 Hz, 1H, H-7), 9.29 (d, J= 2 Hz, 1H, H-9), 12.32 (br. s, 1H, NH), 13.19 (br. s, 1H, NH); MS (m/e): 247 (M⁺, 100%), 191 (46%), 163 (61%), 117 (56%), 90 (58%).

The following example was prepared in an analogous manner from 2,3dichlor -6-trifluoromethylquinoxaline.

EXAMPLE 6

8- Trifluormethyl [1,2,4 ]triazolo [4,3-a ]quinoxaline-1,4 (2H, 5H)-dione

M.p. >350° C. (DSC); ¹H-NMR (DMSO-d₆): δ7.40 (d,J=9 Hz, 1H, H-6), 7.69 (dd, J$_{7-9}$ =9 Hz, J$_{7-9}$ =2Hz, 1H, H-7), 8.83 (d, J=2 Hz, 1H, H-9), 12.11 (br. s, 1H, NH), 13.11 (br. s, 1H, NH).

EXAMPLE 7

8-Chloro-7nitro[1,2,4]triazolo [4,3-a ]quinoxaline-1,4(2H, 5H)-dione

Powdered potassium nitrate (90 mg, 0.89 mmol) was added to a stirred solution of 8-chloro [1,2,4]triazolo [4,3-a]quinoxaline-1,4(2H, 5H)-dione (200 mg, 0.84 mmol) in 2.5 ml of conc. sulfuric acid at 0° C. and stirred at room temperature for 20 min. The mixture was quenched in ice/water (50 ml) and the grey precipitate was collected, dissolved in hot ethanol, treated with decolourising charcoal, filtered hot and concentrated to about 10 ml. After stirring at 0° C. the precipitate was collected, washed with a small amount of cold ethanol and dried in vacuo to give 80 mg (34%) of the title compound; m.p. >400° C. dec. (DSC); ¹H-NMR (DMSO-d₆): δ7.88 (s, 1H, H-6), 8.67 (s, 1H, H-9), 12.15 (br, s, 1H, NH), 13.20 (br,s, 1H, NH); MS (m/e): 283 ((M +2)⁺, 32%), 281 (M⁺, 100%).

The following two examples were prepared in an analogous manner from the appropriate [1,2,4]triazolo [4,3-a]quinoxaline-1,4(2H, 5H)-dione.

EXAMPLE 8

6-Nitro-8-trifluoromethyl [1,2,4]triazolo [4,3-a]quinoxaline-1,4(2H, 5H)-dione

M.p. >300° C. (DSC); $^1$H-NMR (DMSO-d$_6$): $\delta$8.38 (d, J=2 Hz, 1H, H-7), 9.18(d, J=2 Hz, H-9), 11.48 (br. s, 1H, NH). 13.42 (br. s, 1H, NH).

EXAMPLE 9

8-Nitro-7-trifluoromethyl [1,2,4]triazolo [4,3-a]quinoxaline-1,4(2H, 5H)-dione

M.p. >375° C. dec. (DSC); $^1$H-NMR (DMSO-d$_6$): $\delta$7.70 (s, 1H, H-6), 9.16 (s, 1H, H-9), 12.40 (s, 1H, NH), 13.32 (s, 1H, NH).

EXAMPLE 10

7-Chloro [1,2,4]triazolo [4,3-a]quinoxaline-1,4(2H, 5H)-dione

A solution of 20% phosgene in toluene (1.6 ml, 3 mmol) was added to a solution of 0.56 g (2.5 mmol) of 6-chloro-2-hydrazino-3-methoxyquinoxaline (R. Sarges et al. J Med Chem. 33, 2240 (1990)) in 40 ml of dry tetrahydrofuran and the mixture was stirred over night at room temperature. The solvent was removed in vacuo and the solid residue was refluxed for 2.5 h in a mixture of 6 ml of 1N hydrochloric acid and 20 ml of glacial acetic acid. The mixture was cooled and filtered to give a white solid. Washing with acetic acid, water and ethanol and drying in vacuo afforded 172 ml (29%) of the title compound; m.p. >375° C. dec. (DSC) $^1$H-NMR (DMSO-d$_6$): $\delta$7.25 (d, J=2 Hz, 1H, H-6), 7.30 (dd, $J_{8-9}$=9 Hz, $J_{8-6}$=2 Hz, 1H, H-8), 8.51 (d, J=9 Hz, 1H, H-9), 11.87 (br. s, 1H, NH), 13.0 (br. s, 1H, NH) MS (m/e): 238 ((M +2)$^+$, 31%, 236 (M$^+$, 100%), 180 (35%), 152 (78%).

EXAMPLE 11

7-nitro-1-(trifluoromethyl)[1,2,4]triazolo[4,3-a]quinoxalin-4(5H)-one Under nitrogen in a flame-dried flask, 0.82 g (3.4 mmol) of 3-chloro-2-hydrazino- 6-nitroquinoxaline was added to 2.75 ml (36 mmol) of trifluoroacetic acid with stirring at 0° C. The mixture was then heated to 100° C. for 4 h and poured into ice/water. The red precipitate was collected and washed with water. Chromatography on silica gel with ethyl acetate gave 0.22 g (22%) of the pure title compound; m.p. >348° C. dec. (DSC); $^1$H -NMR (DMSO-d$_6$): $\delta$8.04 (d,J=9 Hz, 1H, H-9), 8.21–8.29 (m, 2H, ArH), 12.78 (br. s, 1H, NH); MS (m/e): 299 (M$^+$, 100%).

EXAMPLE 12

A. 1 -Benzyloxy-7-chloro-8-cyanoquinoxaline-2,3(1H, 4H)-dione

To a solution of 2,0 g (~8,4 mmol) 7-chloro-8-cyano-1-hydroxyquinoxaline-2,3(1H,4H)-dione in a mixture of 150 ml ethanol and 175 ml 0,1M phosphate buffer pH 7.4 was added 3.0 g (~17,4 mmol) of benzylbromide. Stirring was continued for 20 h at 24° C. The precipitate was filtered off to give the title compound (2.7 g; 98%), m.p. 227°–229° C.

B. 1 -Benzyloxy-3,7-dichloro-8-cyanoquinoxaline-2,3(1H, 4H)-dione

To a solution of 2.0 g (~6.1 mmol) 1-benzyloxy-7-chloro-8-cyanoquinoxaline- 2,3(1H,4H)-dione in 50 ml of dried N,N-dimethylformamide was added at 0° C. 13.8 ml of 1.93M phosgene in toluene (~26,6 mmol). Stirring was continued at 24° C. for 3H. The evaporated reaction mixture was stirred with water to give the title compound (1.65 g; 79%), m.p. 156°–158° C.

C. 1 -Benzyloxy-7-chloro-8-cyano-3-(ethoxycarbonylhydrazino)-quinoxaline- 2,3(1H,4H)-dione To a solution of 1.5 g (~4,3 mmol) 1-benzyloxy-3,7-dichloro-8-cyanoquinoxaline- 2,3(1H,4H)-dione in 100 ml of acetonitrile was added 2.0 g (~19.2 mmol) of ethyl carbazate. The reaction mixture was refluxed for 3 h, and then evaporated in vacuo to give an oil. Column chromatography with ethyl acetate as eluent gave the title compound (0.9 g; 52%), m.p. 150° C. decomp.

D. 6-Cyano-7-chloro[1,2,4]triazolo[4,3-a]quinoxaline-1,4(2H,5H)-dione

A solution of 0.9 g (~2.2 mmol) 1-benzyloxy-7-chloro-8-cyano- 3-(ethoxycarbonylhydrazino)-quinoxaline-2,3(1H, 4H)-dione in 150 ml of ethanol was hydrogenated at atm. pressure by using 5% Pd-C (0.1 g) as a catalyst. The reaction mixture was filtered and evaporated in vacuo to give the desbenzyl derivative. The crude product was dissolved in 40 ml of N,N-dimethylformamide and added 1.6 g (~6.2 mmol) of triphenylphosphine. Stirring was continued at 100° C. for 20 h. The evaporated reaction mixture was stirred with dichloromethane to give a precipitate. Recrystallization (N,N-dimethyl-formamide-dichloromethane) gave the title compound (0.38; 52%), m.p.>300° C. decomp. $^1$H-NMR (DMSO-d$_6$): $\delta$12.5 (2H, broad signal), 8.7 (1H,d), 7.35 (1H,d).

The following two examples were prepared in an analogous manner from the appropriate 1 -hydroxyquinoxaline-2,3(1H,4H)-dione.

EXAMPLE 13

7-Cyano-8-trifluoromethyl [1,2,4]triazolo [4,3-a ]quinoxaline-1,4 (2H, 5H)-dione M.p.>350° C. (dec.) (DSC); $^1$H-NMR (DMSO-d6): $\delta$7.76 (s, 1H, H-6), 8.98 (s, 1H, H-9), 12.82 (br. s, 2H, 2 NH); IR (KBr): 2237 cm$^{-1}$; MS (m/e): 295 (M$^+$, 100%);

$C_{11}H_4F_3N_5O_2$(295) Calc. C 44.76 H 1.37 N 23.72 Found 44.69 H 1.34 N 23.47

EXAMPLE 14

7-Sulfamoyl-8-trifluoromethyl[1,2,4]triazolo [4,3-a ]quinoxaline-1,4(2H,5H)-dione M.p. >330° C.; $^1$H-NMR (DMSO-d$_6$): $\delta$7.80 (br. s, 2H, NH$_2$), 8.05 (s, 1H, H-6), 9.00 (s, 1 H, H-9), 12.32 (s, 1 H, NH), 13.18 (s, 1 H, NH).

EXAMPLE 15

A. 2,6,7-Trichloroquinoxaline-3 (4H)-one

To a solution of 2.5 g (~10.8 mmol) 6,7-dichloro-quinoxaline-2,3(1H,4H)-dione in 100 ml of dry N,N-dimethylformamide was added at 0° C. 8.5 ml of 1.93 M phosgene in toluene (~16.3 mmol). Stirring was continued at 24° C. for 20 h. Addition of 100 ml H$_2$O gave a precipitate (2.4 g). Purification by column chromatography (silica gel) by using ethyl acetate as eluent gave the title compound (1.5 g; 56%), m.p. >300° C.

B. 2-(Ethoxycarbonylhydrazino)-6,7-dichloro-quinoxalin-3(4H)-one

To a solution of 0.58 g (~2.3 mmol) 2,6,7-trichloroquinoxalin-3(4H)-one in 25 ml of acetonitrile was added 0.27 g (~2.6 mmol) of ethyl carbazate. The reaction mixture was refluxed for 3 h. Cooling to 24° C. gave the title compound (0.62 g; 84%) as a precipitate. M.p. >300° C. decomp.

C. 7,8-Dichloro[1,2,4]triazolo[4,3-a]quinoxaline-1,4(2H, 5H)-dione

A mixture of 0.6 g (~1.9 mmol) 2-(ethoxycarbonylhydrazino)-6,7-di- chloroquinoxaline-3(4H)-one and 25 ml of 1N sodium hydroxide was stirred at 24° C. for 1 h. Addition of 4N hydrochloric acid to pH 2 gave the title compound (0.39 g; 77%) as a precipitate. M.p. >300° C. decomp. $^1$H-NMR (DMSO-d$_6$): δ13.1 (1H,s), 12.0 (1H,s), 8.6 (1H,s), 7.4 (1H,s).

EXAMPLE 16

7-Cyano-8-nitro[1,2,4]triazolo[4,3-a]quinoxaline-1,4(2H, 5H)-dione

7-Cyano[1,2,4]triazolo[4,3-a]quinoxaline-1,4(2H,5H)-dione (0.5 g; 2.2 mmol) was gradually added to 15 ml of nitric acid (100%) at 0°. Stirring was continued at 0° C. for 30 min. and then at 24° C. for 2 H. The reaction mixture was poured into ice-water to give the title compound (0.3 g; 50%), m.p.>400° C. decomp. $^1$H-NMR (DMSO-d$_6$): δ13.4 (1H,s), 12.5 (1H,s), 9.35 (1H,s), 7.75 (1H,s).

EXAMPLE 17

7-Nitro-1 -propyl[1,2.4]triazolo[4,3-a]quinoxaline-4(5H)-one

A mixture of 0.4 g (~1.7 mmol) 3-chloro-2-hydrazino-6-nitroquinoxaline and 4 ml of triethyl orto-n-butyrate was stirred at 100° C. for 1 h. After cooling to 25° C., the precipitate was filtered off to give 0.27 g of the triazolo derivative. A mixture of the crude product and 2 ml of glacial acetic acid was refluxed for 1 h. After cooling to 25° C., the title compound (0.22 g; 48%) was filtered off. M.p. 348° C. decomp. $^1$H-NMR (DMSO-d$_6$): δ12.2 (1 H,s), 8.3–8.0 (3H, m), 3.3 (2H, m), 1.9 (2H, q), 1.1 (3H,t).

The following two examples were prepared in an analogous manner from the appropriate 2(3)-chloro-3(2)-hydrazinoquinoxaline. The 2-Chloro-3-hydrazino- 6-trifluoromethylquinoxaline and 3-chloro-2-hydrazino-6-trifluoromethylquinoxaline isomers were prepared from 2,3-dichloro-6-trifluoromethylquinoxaline by treatment with hydrazine hydrate in dichloromethane, and separated by column chromatography (silica gel) with toluenemethyl acetate (3:1).

EXAMPLE 18

1 -Propyl-7-trifluoromethyl[1,2,4]triazolo[4,3-a]quinoxalin-4(5H)-one

M.p. 292° C. (DSC); $^1$H -NMR (DMSO-d$_6$): δ1.10 (t, J=7 Hz, 3H, CH$_3$), 1.93 (sixtet, J=7 Hz, 2H, CH$_2$), 3.34 (t, J=7 Hz, 2H, CH$_2$), 7.60–7.72 (m, 2H, H-6 +H-8), 8.20 (d, J=9 Hz, 1 H, H-9), 12.2 (br. s, 1H, NH).

EXAMPLE 19

1 -Propyl-8-trifluoromethyl[1,2, 4 ]triazolo [4,3-a ]quinoxaline-4 (5H)-one

M.p. 318° C. (DSC); $^1$H-NMR (DMSO-d$_6$): δ1.09 (t, J=7 Hz, 3H, CH$_3$), 1.91 (sixted, J=7 Hz, 2H, CH$_2$), 3.38 (t, J=7 Hz, 2H, CH$_2$), 7.56 (d, J=9 Hz, 1H, H-6), 7.85 (dd, J$_{7-6}$=9 Hz, J$_{7-9}$ =2 Hz, 1H, H-7), 8.10 (d, J=2 Hz, 1H,H-9), 12.32 (br. s, 1H, NH).

EXAMPLE 20

A. 8-Amino-7-trifluoromethyl[1,2,4]triazolo[4,3-a]quinoxaline-1,4(2H,5H)-dione

A solution of 8-nitro-7-trifluoromethyl[1,2,4]triazolo[4,3-a]quinoxaline-1,4(2H,5H)-dione (5.24 g, 16.6 mmol) in 150 ml of N,N-dimethylformamide and 250 ml of ethanol was hydrogenated at 50 atm. pressure and room temperature for 3 h in the presence of Raney-Ni. The catalyst was removed by filtration and washed with N,N-dimethylformamide. The filtrate was evaporated to dryness and triturated with water and ethanol to give 4.38 g (92%) of the title compound, m.p. >300° C.; $^1$H-NMR (DMSO-d$_6$): δ5.75 (br. s, 2H, NH$_2$), 7.24 (s, 1H, ArH), 8.12 (s, 1H, ArH), 11.50 (br. s, 1 H, NH), 12.92 (br. s, 1H, NH).

B. 8-Cyano-7-trifluoromethyl[1,2,4]triazolo[4,3-a]quinoxaline-1,4(2H,5H)-dione

A solution of 8-amino-7-trifluoromethyl[1,2,4]triazolo[4, 3-a]quinoxaline-1,4(2H,5H)-dione (1.22 g, 4.2 mmol) in 60 ml of conc. hydrochloric acid was diazotised at 0° C. with sodium nitrite (300 mg, 4.3 mmol) in 10 ml of water. After stirring at 0° C. for 40 min the solution was added a solution of sodium hydrogen carbonate (64 g) and potassium tetracyanonickelate (3 g) in 700 ml of water. Stirring was continued for 90 min. at room temperature followed by 50° C. for 20 min. The cooled mixture was extracted with ethyl acetate, and the organic phase was evaporated to dryness. Column chromatography with ethyl acetate afforded 370 mg (29%) of the title compound, m.p. >400° C. (DSC); $^1$H-NMR (DMSO-d$_6$): δ7.70 (s, 1H, H-6), 8.98 (s, 1H, H-9), 12.85 (br. s, 2H, 2NH); IR (KBr): 2238 cm$^{-1}$.

EXAMPLE 21

8-Sulfamoyl-7-trifluoromethyl [1,2, 4 ]triazolo [4, 3-a ]quinoxaline-1,4 (2H, 5H)-dione A solution of 8-amino-7-trifluoromethyl[1,2,4]triazolo[4, 3-a]quinoxaline1,4(2H,5H)-dione (627 mg, 2.2 mmol) in 35 ml of conc. hydrochloric acid and 10 ml of acetic acid was diazotized at 0° C. with sodium nitrite (160 mg, 2.3 mmol) in 3 ml of water. The mixture was stirred at 0° C. for 1 h and poured into a saturated solution of sulfur dioxide in 10 ml of acetic acid containing 50 mg of cupric chloride. The mixture was stirred for 2 h and poured onto 100 g of ice. The crude 8-chlorosulfonyl-7-trifluoromethyl[1,2,4]triazolo[4,3-a]quinoxaline-1,4(2H,5H)-dione was isolated by flitration, dried and then dissolved in 50 ml of tetrahydrofuran. Ammonia gas was bubbled through the solution for 10 min., and the mixture was stirred for 1 h at room temperature. The precipitate was filtered off and treated with 4 M hydrochloric acid to give 200 mg (26%) of the title compound, m.p. >350° C. (DSC); $^1$H-NMR (DMSO-d$_6$): δ7.69 (s, 1H, H-6), 7.77 (s, 2H, NH$_2$), 9.35 (s, 1H, H-9), ca. 12.6 (very br. s, 2H, 2NH); MS (m/e): 349 (M$^+$, 100%); C$_{10}$H$_6$F$_3$N$_5$O$_4$S (349) Calc. C 34.39 H 1.73 N 20.05 S 9.18 Found C 34.17 H 1.76 N 19.60 S 9.15

We claim:

1. A method of treating an indication selected from the group consisting of cerebral ischemia, anoxia, hypoglycemia, and head and spinal cord trauma, in a subject in need thereof, comprising administering an effective amount of a compound of formula I

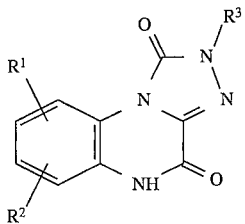

(I)

wherein

R[1] and R[2] are independently hydrogen, $C_{1-6}$-alkyl, halogen, $NO_2$, $NH_2$, CN, $CF_3$, $SO_2NR^4R^5$ wherein R[4] and R[5] are independently hydrogen or $C_{1-6}$-alkyl, or COR[6] wherein R[6] is $C_{1-6}$-alkyl; and R[3] is hydrogen, $C_{1-6}$-alkyl or $CF_3$; or pharmaceutically acceptable salt thereof.

2. A method of treating an indication selected from the group consisting of cerebral ischemia, anoxia, hypoglycemia, and head and spinal cord trauma, in a subject in need thereof, comprising administering an effective amount of a compound of formula II

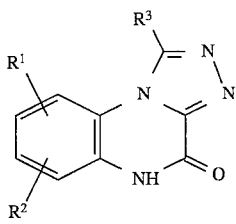

(II)

wherein

R[1] and R[2] are independently hydrogen, $C_{1-6}$-alkyl, halogen, $NO_2$, $NH_2$, CN, $CF_3$, $SO_2NR^4R^5$ wherein R[4] and R[5] are independently hydrogen or $C_{1-6}$-alkyl, or COR[6] wherein R[6] is $C_{1-6}$-alkyl; and R[3] is hydrogen, $C_{1-6}$-alkyl, or $CF_3$; or pharmaceutically acceptable salt thereof.

3. A compound of formula I

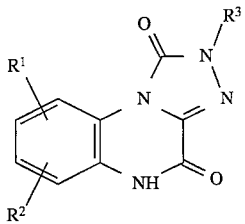

(I)

wherein

R[1] and R[2] are independently hydrogen, halogen, $NO_2$, $NH_2$, CN, $CF_3$, $SO_2NR^4R^5$ wherein R[4] and R[5] are independently hydrogen or $C_{1-6}$-alkyl, or COR[6] wherein R[6] is $C_{1-6}$-alkyl, provided that at least one of R[1] and R[2] is not hydrogen; and R[3] is hydrogen or $CF_3$; or a pharmaceutically acceptable salt thereof.

4. A compound of formula II

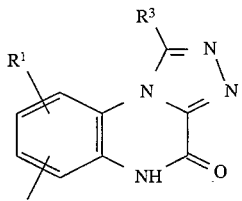

(II)

wherein

R[1] and R[2] are independently hydrogen, halogen, $NO_2$, $NH_2$, CN, $CF_3$, $SO_2NR^4R^5$ wherein R[4] and R[5] are independently hydrogen or $C_{1-6}$-alkyl, COR[6], wherein R[6] is $C_{1-6}$-alkyl, provided that at least one of R[1] and R[2] is not hydrogen; and R[3] is hydrogen, $C_{1-6}$-alkyl or $CF_3$; or a pharmaceutically acceptable salt thereof.

5. The compound according to claim 4, wherein R[3] is trifluoromethyl or proply.

6. A compound according to claim 4 which is
1-trifluoromethyl-7-nitro[1,2,4]triazolo[4,3-a]quinoxaline-4(5H)-one;
1-propyl-7-nitro[1,2,4]triazolo[4,3-a]quinoxaline-4(5H)-one;
1-propyl-7-trifluoromethyl[1,2,4]triazolo[4,3-a]quinoxaline-4(5H)-one;
1-propyl-8-trifluoromethyl[1,2,4]triazolo[4,3-a]quinoxaline-4(5H)-one; or a pharmaceutically acceptable salt thereof.

7. A pharmaceutical composition comprising an effective amount of a compound according to claim 4 and a pharmaceutically acceptable carrier or diluent.

8. A pharmaceutical composition according to claim 7 in the form of a dosage unit containing about 10–200 mg of the compound.

9. A method according to claim 1 wherein the indication is anoxia.

10. A method according to claim 2 wherein the indication is anoxia.

11. The compound according to claim 3, wherein R[1] and R[2] are independently hydrogen, chloro, $NO_2$, $NH_2$, CN, $CF_3$, or $SO_2NH_2$, provided that at least one of R[1] and R[2] is not hydrogen.

12. The method according to claim 1 wherein the compound is
8-chloro-7-nitro[1,2,4]-triazolo[4,3-a]quinozalin-1,4(2H,5H)-dione;
7-cyano-8-trifluoromethyl[1,2,4]-triazolo[4,3-a]quinozalin-1,4(2H,5H)-dione;
or
a pharmaceutically acceptable salt thereof.

13. A method according to claim 1, wherein the indication is cerebral ischemia.

14. A method according to claim 1, wherein the indication is hypoglycemia.

15. A method according to claim 1, wherein the indication is head and spinal cord trauma.

16. The compound according to claim 3, wherein R[3] is hydrogen.

17. A compound according to claim 3 which is
8-chloro[1,2,4]triazolo[4,3-a]quinoxaline-1,4(2H,5H)-dione;
7-nitro[1,2,4]triazolo[4,3-a]quinoxaline-1,4(2H,5H)-dione;

7-trifluoromethyl[1,2,4]triazolo[4,3-a]quinoxaline-1,4(2H,5H)-dione;

7-cyano[1,2,4]triazolo[4,3-a]quinoxaline-1,4(2H,5H)-dione;

8-nitro[1,2,4]triazolo[4,3-a]quinoxaline-1,4(2H,5H)-dione;

8-trifluoromethyl[1,2,4]triazolo[4,3-a]quinoxaline-1,4(2H,5H)-dione;

6-nitro-8-trifluoromethyl[1,2,4]triazolo[4,3-a]quinoxaline-1,4(2H,5H)-dione;

8-nitro-7-trifluoromethyl[1,2,4]triazolo[4,3-a]quinoxaline-1,4(2H,5H)-dione;

7-chloro[1,2,4]triazolo[4,3-a]quinoxaline-1,4(2H,5H)-dione;

6-cyano-7-chloro[1,2,4]triazolo[4,3-a]quinoxaline-1,4(2H,5H)-dione;

7-sulfamoyl-8-trifluoromethyl[1,2,4]triazolo[4,3-a]quinoxaline-1,4(2H,5H)dione;

7,8-dichloro[1,2,4]triazolo[4,3-a]quinoxaline-1,4(2H,5H)-dione;

7-cyano-8-nitro[1,2,4]triazolo[4,3-a]quinoxaline-1,4(2H,5H)-dione;

8-amino-7-trifluoromethyl[1,2,4]triazolo[4,3-a]quinoxaline-1,4(2H,5H)-dione;

8-cyano-7-trifluoromethyl[1,2,4]triazolo[4,3-a]quinoxaline-1,4(2H,5H)-dione;

8-sulfamoyl-7-trifluoromethyl[1,2,4]triazolo[4,3-a]quinoxaline-1,4(2H,5H)-dione; or a pharmaceutically acceptable salt thereof.

18. A compound according to claim 3 which is 8-chloro-7-nitro[1,2,4]triazolo[4,3-a]quinoxaline-1,4(2H, 5H)-dione or a pharmaceutically acceptable salt thereof.

19. A compound according to claim 3 which is 7-cyano-8-trifluoromethyl [1,2,4]triazolo[4,3-a]quinoxaline-1,4(2H, 5H)-dione or a pharmaceutically acceptable salt thereof.

20. A pharmaceutical composition comprising an effective amount of a compound according to claim 3, and a pharmaceutically acceptable carrier or diluent.

21. A pharmaceutical composition according to claim 20 in the form of a dosage unit containing about 10–200 mg of the compound.

22. A method according to claim 2, wherein the indication is cerebral ischemia.

23. A method according to claim 2, wherein the indication is hypoglycemia.

24. A method according to claim 2, wherein the indication is head and spinal cord trauma.

* * * * *